United States Patent
Vu Thi et al.

(10) Patent No.: US 10,180,238 B2
(45) Date of Patent: Jan. 15, 2019

(54) LIGHTING DEVICE HAVING A COMPACT LIGHTING DOME FOR FORMING AN ILLUMINATION SPOT OF VARIABLE DIAMETER AND OF VARIABLE COLOR TEMPERATURE

(71) Applicant: MAQUET SAS, Ardon (FR)

(72) Inventors: Minh Hong Vu Thi, Orléans (FR); Cécilia Valteau, Ligny le Ribault (FR)

(73) Assignee: MAQUET SAS, Ardon (FR)

( * ) Notice: Subject to any disclaimer, the term of this patent is extended or adjusted under 35 U.S.C. 154(b) by 422 days.

(21) Appl. No.: 15/168,738

(22) Filed: May 31, 2016

(65) Prior Publication Data
US 2016/0356458 A1 Dec. 8, 2016

(30) Foreign Application Priority Data
Jun. 2, 2015 (FR) ...................... 15 54975

(51) Int. Cl.
*F21Y 103/33* (2016.01)
*F21W 131/205* (2006.01)
(Continued)

(52) U.S. Cl.
CPC .............. *F21V 13/04* (2013.01); *A61B 90/30* (2016.02); *F21S 8/043* (2013.01); *F21V 5/04* (2013.01);
(Continued)

(58) Field of Classification Search
CPC .............. F21Y 2103/33; F21Y 2105/12; F21Y 2107/00; F21Y 2113/10; F21V 3/00; F21W 2131/20
(Continued)

(56) References Cited

U.S. PATENT DOCUMENTS

| 5,913,599 A | 6/1999 | Smith et al. |
| 2006/0007538 A1* | 1/2006 | Robinson ............. G02B 27/102 359/487.04 |

(Continued)

FOREIGN PATENT DOCUMENTS

| EP | 2799764 A1 | 11/2014 |
| FR | 1025846 A | 4/1953 |

(Continued)

OTHER PUBLICATIONS

French Search Report in corresponding French Patent Application No. 1554975, dated Nov. 12, 2015.

*Primary Examiner* — William J Carter
(74) *Attorney, Agent, or Firm* — Edell, Shapiro & Finnan, LLC

(57) ABSTRACT

A lighting device for illuminating an operative field comprises, in an axial lighting dome, a first ring of LEDs at a first color temperature, and a second ring of LEDs at a second color temperature different from said first color temperature, and an annular facetted mirror having semi-reflective facets and arranged about the same axis as said rings of LEDs. Collimation optical systems are provided between each ring of LEDs and the annular facetted mirror having semi-reflective facets. The annular facetted mirror having semi-reflective facets mixes the collimated light beams emitted by the two rings of LEDs coupled to the collimators, and forms first and second collimated resulting mixed light beams having the same intermediate color temperature. An annular facetted mirror having plane facets surrounds the annular facetted mirror having semi-reflective facets so as to reflect the first collimated resulting mixed light beam to combine it with said second collimated resulting mixed light beam in the operative field in a certain superposition configuration in (Continued)

a superposition plane in which an illumination spot is formed.

10 Claims, 3 Drawing Sheets

(51) Int. Cl.

| | |
|---|---|
| F21V 13/04 | (2006.01) |
| F21V 5/04 | (2006.01) |
| F21V 7/04 | (2006.01) |
| F21V 7/05 | (2006.01) |
| F21V 7/22 | (2018.01) |
| A61B 90/30 | (2016.01) |
| F21S 8/04 | (2006.01) |
| F21V 7/00 | (2006.01) |
| G02B 27/30 | (2006.01) |
| G02B 19/00 | (2006.01) |
| G02B 27/14 | (2006.01) |
| F21Y 115/10 | (2016.01) |
| F21Y 107/00 | (2016.01) |
| F21Y 113/13 | (2016.01) |
| H05B 33/08 | (2006.01) |

(52) U.S. Cl.
CPC ............... *F21V 7/00* (2013.01); *F21V 7/048* (2013.01); *F21V 7/05* (2013.01); *F21V 7/22* (2013.01); *G02B 19/0019* (2013.01); *G02B 19/0066* (2013.01); *G02B 27/143* (2013.01); *G02B 27/145* (2013.01); *G02B 27/30* (2013.01); *A61B 2090/309* (2016.02); *F21W 2131/205* (2013.01); *F21Y 2103/33* (2016.08); *F21Y 2107/00* (2016.08); *F21Y 2113/13* (2016.08); *F21Y 2115/10* (2016.08); *H05B 33/0857* (2013.01)

(58) Field of Classification Search
USPC .................................................. 362/235, 804
See application file for complete search history.

(56) References Cited

U.S. PATENT DOCUMENTS

| | | | |
|---|---|---|---|
| 2008/0174868 A1* | 7/2008 | Schuck | G02B 6/0096 359/485.06 |
| 2010/0045896 A1* | 2/2010 | Shikii | G02B 27/106 349/62 |
| 2011/0069485 A1* | 3/2011 | Jacobi | F21V 7/0033 362/235 |
| 2011/0075420 A1* | 3/2011 | Van Gorkom | F21V 13/10 362/235 |
| 2014/0328045 A1 | 11/2014 | Valteau et al. | |

FOREIGN PATENT DOCUMENTS

| | | |
|---|---|---|
| FR | 2194915 A1 | 3/1974 |
| FR | 2339129 A2 | 8/1977 |
| JP | H02187739 A | 7/1990 |
| JP | 2008253744 A | 10/2008 |
| WO | 2014087088 A1 | 6/2014 |

* cited by examiner

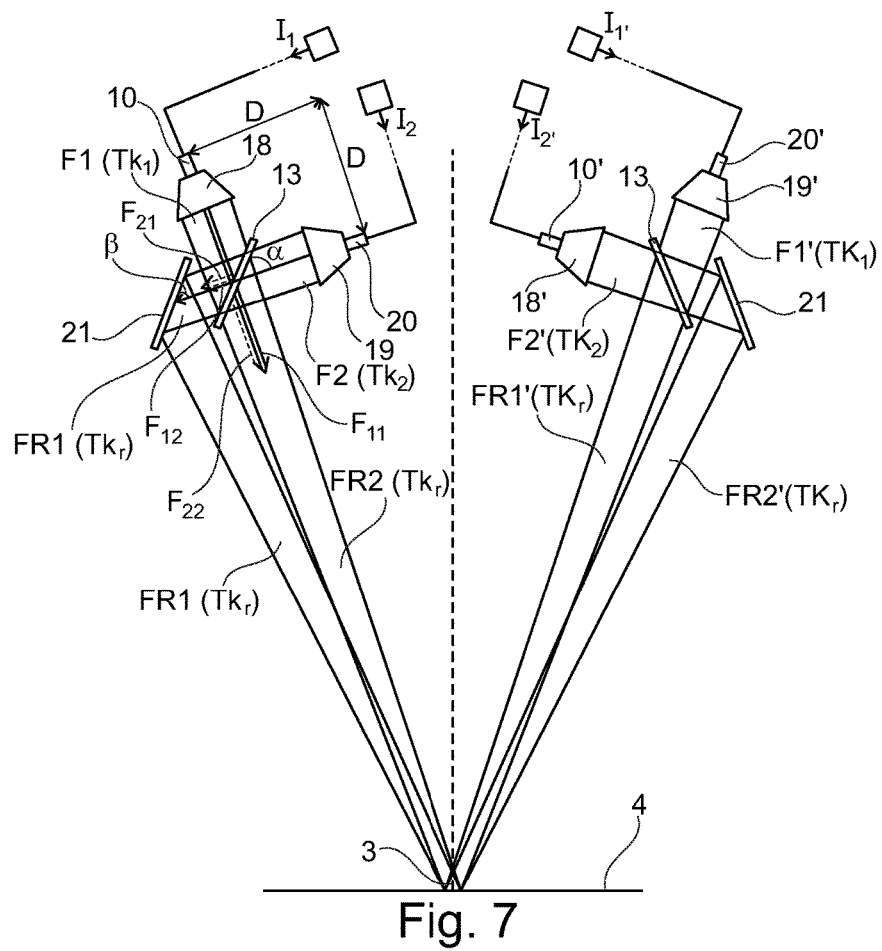
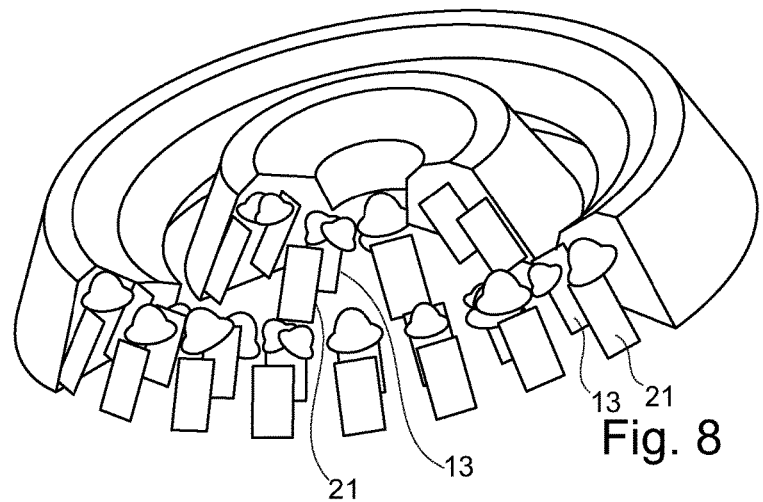

LIGHTING DEVICE HAVING A COMPACT LIGHTING DOME FOR FORMING AN ILLUMINATION SPOT OF VARIABLE DIAMETER AND OF VARIABLE COLOR TEMPERATURE

CROSS REFERENCE TO RELATED APPLICATIONS

This application claims foreign priority under 35 U.S.C. §119(a)-(d) to Application No. FR 1554975 filed on Jun. 2, 2015, the entire contents of which are hereby incorporated by reference.

FIELD OF THE INVENTION

The invention relates to the field of lighting devices, and in particular to a lighting device having an axial lighting dome for illuminating a medical operative field.

BACKGROUND

In a medical environment, and in particular in an operating theater, the lighting conditions should be appropriate for enabling a user, e.g. a surgeon or a physician, to work properly. In addition, good lighting should comply with certain standards and should deliver light having a color rendering index (CRI or $R_a$) lying in the range 85 to 100, and a color temperature lying in the range 3000 Kelvin (K) to 6700 K. More precisely, the term "color temperature" of light is used herein to mean the equivalent color temperature evaluated in conventional manner on the basis of the (x,y) chromaticity coordinates of the spectrum of the light in a chromaticity diagram of the International Lighting Commission (CIE).

In addition, in a medical environment, good lighting should offer uniform illumination, and high optical efficiency, without creating colored shadows in the field of illumination. Good lighting should also enable the surgeon to vary the color temperature and/or size of the illumination spot so as to adapt it to suit the surgeon's needs.

In addition, in an operating theater, the lighting device generally has a base fastened to the ceiling and from which an articulated arm extends that carries a lighting dome in which a plurality of lighting modules are disposed. Thus, it is desirable to achieve maximum compactness for the lighting dome above the operative field in order to make it easy for the user to handle the lighting dome.

The Applicant's Document EP 2 799 764 discloses a lighting device for forming an illumination spot of variable diameter and of variable color temperature. That device also makes it possible, by means of a beam splitter, to mix the white light beams of two different color temperatures coming from two white light sources so as to generate resulting mixed light beams at an intermediate color temperature. The optical system of that lighting device comprises a plurality of optical elements for focusing and combining the mixed light beams and for forming an illumination spot at an intermediate color temperature on the field of illumination. Those optical elements are constituted by an elliptical reflector and by a lens, which reflector and lens may be mounted to move relative to the beam splitter. In addition, in that lighting device, in order to reduce the divergence of the white light beams coming from the light sources, lenses are installed between the light sources and the beam splitter. That lighting device suffers from the drawbacks firstly of including a multitude of massive optical elements to be incorporated into the lighting dome, thereby making the structure more complex and heavier, and secondly of including an elliptical reflector, which is an optical part that is of costly and complex technical design.

SUMMARY

An object of the invention is thus to remedy those drawbacks by proposing a lighting device having a lighting dome that is easier to handle and that is of low cost, while also offering uniform illumination, and high optical efficiency, without creating colored shadows in the field of illumination, and while allowing the illumination color temperature to be varied and also allowing the size of the illumination spot to be varied.

To this end, the invention provides a lighting device for illuminating an operative field, the lighting device comprising, in an axial lighting dome, a first ring of light-emitting diodes (LEDs) suitable for emitting a first light beam at a first color temperature, and a second ring of LEDs about the same axis as the first ring of LEDs and suitable for emitting a second light beam at a second color temperature different from the first color temperature, and an annular facetted mirror having semi-reflective facets and arranged about said axis for mixing the light beams emitted by the two rings of LEDs and for forming two resulting mixed light beams having the same intermediate color temperature lying between the first color temperature and the second color temperature, and an annular optical system that surrounds the annular facetted mirror having semi-reflective facets so as to reflect the first resulting mixed light beam onto the operative field to combine it with the second resulting mixed light beam in a certain superposition configuration in a superposition plane in which an illumination spot is formed at the intermediate color temperature, said lighting device being characterized in that said annular optical system that surrounds said annular facetted mirror having semi-reflective facets is a total reflection annular facetted mirror having plane facets that are substantially geometrically similar to the semi-reflective facets, and in that collimation optical systems are provided between each ring of LEDs and the annular facetted mirror having semi-reflective facets.

With this arrangement, the light beams coming from the LEDs and reaching the annular facetted mirror having semi-reflective facets are high-intensity because they are collimated as soon as they exit from the LEDs. Thus, compared with the prior art, the lighting dome of the present invention no longer has a massive lens between the light sources and the annular facetted mirror having semi-reflective facets. In addition, the total reflection annular mirror no longer participates in constructing the high-intensity beam, but rather serves merely to deflect it. An annular facetted mirror having plane facets is inexpensive to manufacture. The number of optical parts in the axial lighting dome of the present invention is lower than in the prior art device. The lighting dome no longer needs a lens downstream from the annular facetted mirror having semi-reflective facets in order to combine, on the operative field, the second resulting mixed light beam with the first resulting mixed light beam.

The lighting device of the invention may advantageously have the following features:
  the collimation optical systems are lenses;
  the collimation optical systems are collimators;
  the collimation optical systems are hybrid reflectors;
  an electrical power supply is provided for feeding currents to said LEDs and for modulating said currents;

in the first ring of LEDs, the LEDs are coupled in alternating manner to a first collimation optical system and to a second collimation optical system, the second collimation optical system being different from the first collimation optical system, and, in the second ring of LEDs, the LEDs are coupled in alternating manner to a third collimation optical system and to a fourth collimation optical system, the first and third collimation optical systems being identical, and the second and fourth collimation optical systems being identical, so that they form respectively a first illumination spot and a second illumination spot, the two spots being of different diameters; with this arrangement, it is possible to modulate the diameter of the illumination spot without any mechanical movement in the lighting device, and in particular with light sources that are static relative to the beam splitter, thereby simplifying the construction of the lighting device while also keeping the illumination constant by controlling the magnitudes of the feed currents in the light sources;

the electrical power supply for feeding currents to the LEDs, and for modulating the currents makes it possible to modify the size of the illumination spot and/or to modify the color temperature of the illumination spot; and the electrical power supply is also arranged to modulate said currents in such a manner as to form an illumination spot at a constant illumination level.

With this arrangement, the thickness, the complexity of the structure and the weight of the dome are reduced, while also keeping the possibility of varying the temperature of the illumination spot and of modifying the diameter of the illumination spot. The variation in the color temperature of the illumination spot is obtained by controlling the magnitudes of the feed currents in the LED light sources.

BRIEF DESCRIPTION OF THE DRAWINGS

The present invention can be better understood and other advantages appear on reading the following detailed description of embodiments given by way of non-limiting example and with reference to the accompanying drawings, in which:

FIG. 7 is a diagram of the optical system and of the light sources for forming an illumination spot on the operative field in an embodiment of the invention; and FIG. 8 is a diagram showing the light sources and the optical system in another embodiment of the lighting device of the invention.

DETAILED DESCRIPTION

Figure 1:
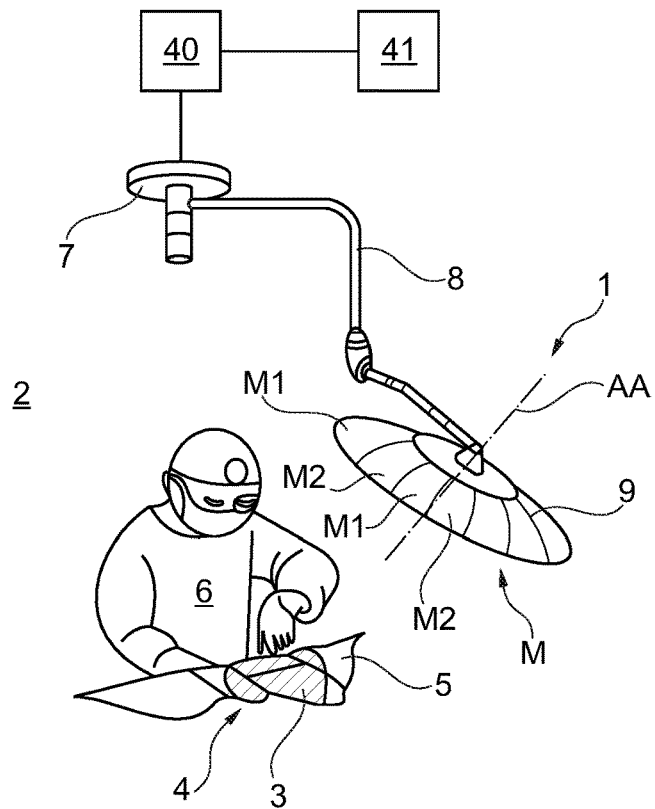
FIG. 1 is a perspective view of a lighting device of the invention that is used in an operating theater.

With reference to FIG. 1, the lighting device 1 of the invention is, in particular, designed to be used in an operating theater 2 for forming an illumination spot 3 (shown diagrammatically by shading) in an operative field 4, e.g. on the body of a patient 5 being operated on by a surgeon 6. In this example, and in known manner, the lighting device 1 has a base 7 that is fastened to the ceiling of the operating theater 2 and from which an articulated arm 8 extends that carries a lighting dome 9 in which there are disposed, for example, a plurality of lighting modules M that may be different, and that are provided in this example with LEDs (not shown in this figure), each of which modules, in this example, is in the form of a quarter of the dome so as to deliver an illumination spot 3 that is centered on the illumination axis AA of the dome. The operative field 4 may be situated in the range 0.8 meters (m) from the lighting dome 9 to 1.6 m from said lighting dome. The illumination spot 3 may have a diameter lying in the range 5 centimeters (cm) to 30 cm.

The lighting device 1 of the invention is designed to form an illumination spot 3 of variable size and of variable color temperature using the light modules M, each light module having two light sources having different color temperatures, e.g. two white LEDs disposed symmetrically relative to a beam splitter. More particularly, said illumination spot is formed by superposing illuminations that are centered on the axis AA and that are produced by the different light modules M.

In this example, the light sources in the different modules M1, M2 are fed selectively and individually with current by an electrical power supply unit 40 coupled to a monitoring and control unit 41.

Figure 2:
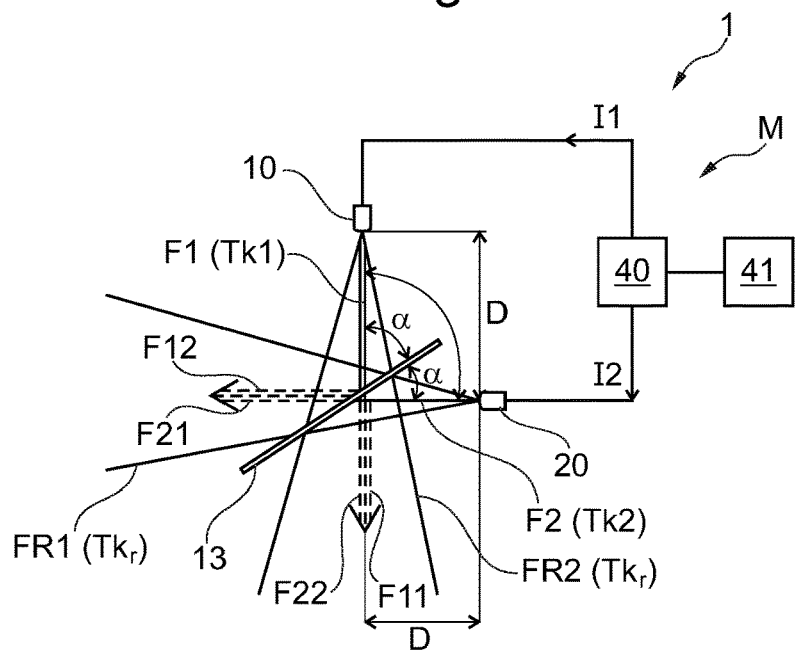
FIG. 2 is a diagram showing how the beam splitter is mounted.

The principle of splitting the light beams produced by two LEDs in a light module M is known from the prior art. As is shown in FIG. 2, the first LED 10 is suitable for emitting a first light beam F1 (shown diagrammatically by a double uninterrupted line) having a first color temperature Tk1. The second LED 20 is suitable for emitting a second light beam F2 (shown diagrammatically by a single uninterrupted line) having a second color temperature Tk2 that is different from the first color temperature Tk1. As shown in FIG. 2, the first and second LEDs 10, 20 are angularly positioned so that the median axes of the beams F1, F2 are angularly positioned at 90° relative to each other, and it can thus be understood that said LEDs are disposed symmetrically relative to the beam splitter 13.

For example, the beam splitter 13 is a high-efficiency dichroic or semi-reflective mirror that is spectrally neutral and that includes a backing plate (made of glass or of a synthetic material) covered with a plurality of thin layers (by optical treatments that can be performed in vacuum equipment or by a sol-gel process). The beam splitter 13 is suitable for splitting each of the first and second beams F1, F2 into a first beam portion F11, F21 (shown diagrammatically respectively by an uninterrupted double line and by an uninterrupted single line) that is transmitted by the beam splitter 13, and into a second beam portion F12, F22 (diagrammatically shown by a dashed double line and by a dashed single line) that is reflected by the beam splitter 13. The beam splitter 13 should make it possible to split each beam F1, F2 with a theoretical yield of 100%, i.e. without any loss, comprising, for example, 50% in reflection and 50% in transmission, or, for example, 30% in reflection and 70% in transmission.

Generally, the beam splitter 13 is disposed at equal distance D from the LEDs 10, 20 and forms the same angle α of 45° with each of the beams F1, F2. In addition, the beam splitter 13 and the LEDs 10, 20 are arranged three-dimensionally so that the first beam F1 and the second beam F2 reach the beam splitter 13 opposite from each other, on either side of the beam splitter 13. Thus, the second portion F12 of the first beam F1 is superposed on or is combined with said first portion F21 of the second beam F2 so as to form a first resulting beam FR1 having a resulting intermediate color temperature Tkr that lies between the first and second color temperatures Tk1, Tk2. In addition, the first portion F11 of the first beam F1 is superposed on or is combined with said second portion F22 of the second beam F2 so as to form a second resulting beam FR2 having the same resulting color temperature Tkr.

In order to cause the color temperature to vary, the LEDs 10, 20 are connected electrically to an electrical power supply 40 coupled to a monitoring and control unit (MCU) 41 suitable for controlling the electrical power supply 40 so as to feed the first LED 10 with a first electric current I1 and so as to feed the second LED 20 with a second electric current I2 that may be different from I1.

The electrical power supply 40 may be in the form of a single electrical power supply for all of the LEDs of the modules M or in the form of two distinct electrical power supplies selectively and respectively feeding all of the LEDs 10 and all of the LEDs 20. It is known that the light flux from an LED depends on the magnitude of the current that is passing through it. In order to modulate the color temperature, the electrical power supply 40 is controlled by the MCU 41 in such a manner as to modulate the magnitudes of the first and second electric currents I1, I2 on the principle of communicating vessels.

Figure 3:
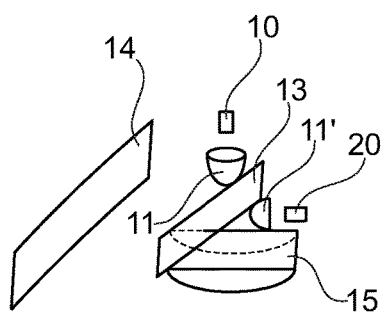
FIG. 3 is a diagrammatic perspective view of the optical elements to be mounted in a prior art lighting dome.

FIG. 3 shows the LEDs 10, 20, the beam splitter 13, and the optical means of a prior art light module for forming the illumination spot in the working plane. Each light module has an elliptical reflector 14, a lens 15, and two lenses 11, 11' that are arranged in the lighting dome so as to focus the beams FR1 and FR2 together and combine them in a superposition plane so as to form the illumination spot. The lenses 11, 11' are positioned between each LED and the beam splitter to collect maximum light flux coming from the LED, and also to reduce the divergence of the beam. With the use of the lenses 11, 11', the virtual image of the LEDs 10, 20 coincides with the object focal point of the elliptical reflector 14 and of the lens 15.

Figure 4:
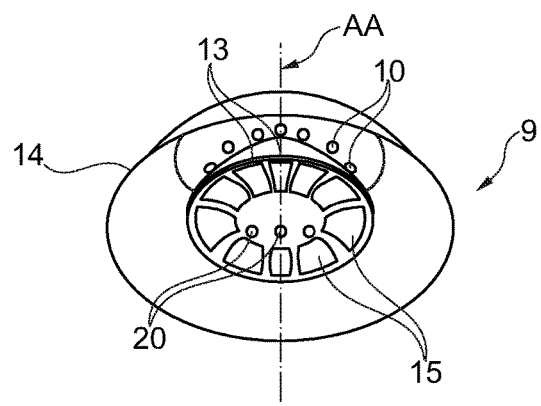
FIG. 4 is a diagrammatic perspective view of the optical elements as arranged in a prior art lighting dome.

FIG. 4 also shows a prior art axial lighting dome in which a plurality of light modules are distributed about the illumination axis. The LEDs 10 of the light modules M form a first ring about the illumination axis AA, and the LEDs 20 of said light modules M form a second ring about the axis AA so that the two rings are about the same axis. Also in the dome 9, there exist a series of beam splitters 13 distributed about the illumination axis AA and that form a ring of beam splitters about the same axis as the rings of LEDs 10, 20, as shown in FIG. 4.

It is known that, with an axial lighting dome of this type, it is possible to form an illumination spot 3 with a variable color temperature Tkr lying in the range Tk1 to Tk2 by controlling the magnitudes of the feed currents in the LEDs 10, 20.

It is also known that with a prior art axial lighting dome of the type described above, it is possible to vary the diameter of the lighting spot by varying the arrangement of the LEDs and/or of the optical system relative to the beam splitter, or by controlling the magnitudes of the feed currents in the LEDs.

In order to have high effectiveness, an elliptical reflector is complex and costly to manufacture, because it is generally prepared by using plastics injection-molding technology. Preparing the injection mold is a costly investment. The plastics part must then be treated in a vacuum in order to deposit successively a keying layer and then a plurality of metal layers. Since the elliptical reflector is not a plane part, depositing the metal layers uniformly is complex.

The elliptical reflector may also be made of aluminum using the spinning technique, that technology being costly and being known to suffer from shape that is less precise than with injection molding of plastics. In addition, since the elliptical reflector is not circularly symmetrical, it is necessary to start with a circularly symmetrical part that must then be cut, which involves complex industrial operations and might give rise to degradation. Finally, the reflection is only 80%.

It should also be noted that, in the prior art axial lighting dome, in order to give a larger light spot, the virtual image of the LED is shifted away from the object image of the elliptical reflector 14 and of the lens 15. This principle generates a light spot that is not round, since it comes from the side of the elliptical reflector, and, as a result, when this spot is superposed on the spot coming from the lens 15, the final light spot is not uniform.

In spite of the presence of the lenses 11, 11' positioned between each LED and the beam splitter 13, the thickness of the axial lighting dome remains large because use is made of a combination of optical systems comprising the lens 11 and the elliptical reflector 14 or the lens 11' and the elliptical reflector 15 as focusing optical systems. The size of the optical systems 14 and 15 is very large in order to capture as much of the resulting light beams as possible. The weight and the volume of the dome are also increased by the presence of these multiple optical elements.

Figure 5:
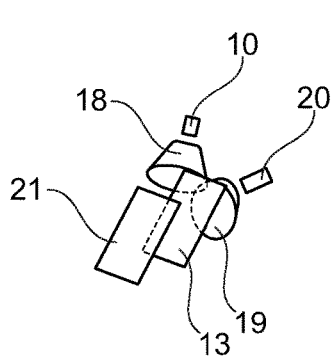
FIG. 5 is a diagrammatic perspective view of the optical elements to be mounted in an embodiment of a lighting dome of the invention.
Figure 6:
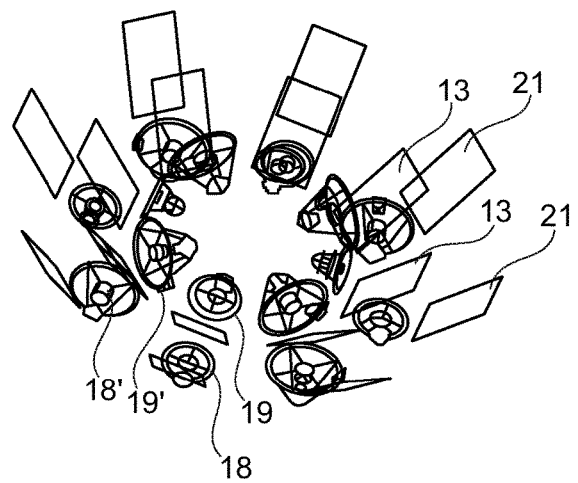
FIG. 6 is a diagrammatic perspective view of the optical elements as arranged in an embodiment of a lighting dome of the invention.

FIGS. 5 and 6 show the elements making up the optical system in a light module, and their possible arrangement in the axial lighting dome of the invention.

FIG. 5 shows two LEDs 10, 20, each having a respective collimation optical system placed in front of it, which system is a collimator 18, 19 in this example, whereby the light beams emitted by the LEDs are focused before they reach the beam splitter 13. A plane facetted mirror 21 is arranged in the dome so as to be capable of totally reflecting, towards the operative field, one of the light beams already focused and beam of mixed resulting light that is the result of the beam splitter 13 mixing two light beams and that is already focused.

FIG. 6 shows the arrangement of an embodiment of an axial lighting dome for forming an illumination spot 3 of variable diameter and of variable temperature color. In this embodiment, a first ring of LEDs 10 and a second ring of LEDs 20 are arranged about the same axis. The beam splitter 13 is an annular facetted mirror having semi-reflective facets and also about said axis. Collimators 18, 19 are arranged between each ring of LEDs 10, 20 and the beam splitter 13. As can also be seen in FIG. 6, a total-reflection annular facetted mirror having plane facets 21 surrounds the annular facetted mirror having semi-reflective facets 13. The facets of the annular facetted mirror having plane facets 21 are substantially geometrically similar (substantially homothetic) to the facets of the annular mirror having semi-reflective facets 13.

The beam splitter 13 may also be constituted by a plurality of plane semi-reflective mirrors disposed annularly.

The total reflection mirror 21 may be made up of a plurality of one-facet plane mirrors disposed annularly.

FIG. 7 shows the configuration of the optical elements included in two lighting modules incorporated into an axial lighting dome of the invention having an axial illumination axis AA.

A first light module comprises two LEDs 10, 20. Preferably, the first and second LEDs 10, 20 that are used are geometrically identical and have different color temperatures Tk1, Tk2, and they come from the same supplier, have the same housings, have the same electronic chips, and require the same type of power supply. The LEDs 10, 20 are disposed at equal distance from the facetted mirror having semi-reflective facets 13, the first LED 10 being turned through 90° relative to the second LED 20. In front of each of the LEDs 10, 20 two identical collimation optical systems 18, 19 are arranged, at equal distance from the LEDs 10, 20. Thus, as shown in this example, two collimated light beams F1 at Tk1 and F2 at Tk2 are generated. On the beam splitting principle described above, the beams F1 and F2 are split by the facetted mirror having semi-reflective facets 13, inclined at an angle α of 45°, to produce two resulting mixed light beams FR1, FR2, having the same color temperature Tkr intermediate between Tk1 and Tk2. In accordance with the invention, the resulting mixed light beams FR1 and FR2 are collimated. The collimation optical system may be a collimation lens, a collimator, or a hybrid reflector, or any other component performing an intensive collimation function. Thus, in accordance with the invention, no optical system is necessary to send onto the operative field 4 the resulting collimated mixed light beam FR2 to form the illumination spot 3. In accordance with the invention, only a facetted mirror having plane facets is arranged to deflect the resulting mixed light beam FR1 onto the operative field, in such a manner that it is superposed on the resulting mixed light beam FR2 so that together they form the illumination spot 3. For this purpose, the facetted mirror having plane facets is inclined at an angle β lying in the range 37° to 57° so that said mirror is a total reflection mirror.

FIG. 7 shows a second light module having two identical light sources having LEDs 10', 20' that are coupled to two identical collimation optical systems 18', 19', generating two collimated light beams respectively F1' of color temperature Tk1 and F2' of color temperature Tk2, different from Tk1. The beams F1' and F2' are split by the facetted mirror having semi-reflective facets 13 that is inclined at an angle α of 45° to produce two collimated resulting mixed light beams FR1', FR2' having the same intermediate color temperature Tkr, identical to the intermediate color temperature of the first module and lying between Tk1 and Tk2. The module is arranged in such a manner that the collimated resulting mixed light beam FR2' is superposed on the illumination spot 3. The resulting mixed light beam FR2' is deflected by the facetted mirror having plane facets that is inclined at an angle β lying in the range 37° to 57° in such a manner that it is superposed on the resulting mixed light beam FR1', FR1 and FR2 so that together they form the illumination spot 3.

It can be understood firstly that, in accordance with the invention, in the axial lighting dome, the entire collimation function takes place very close to the LEDs due to the presence of the collimation optical systems 18, 19. Thus, by generating collimated light beams, which are beams diverge less than in the system described in the prior art, it is possible to use a beam splitter having a semi-reflective mirror that is of smaller size than in the prior art.

In addition, since the first resulting mixed light beam FR1 at the outlet of the beam splitter is collimated, it is advantageous to be able to replace the elliptical reflector of the system described in the prior art by a plane mirror 21 so as to reflect said mixed light beam onto the operative field.

In accordance with the invention, the axial lighting dome can be made more compact by reducing the distance between the LEDs and the annular facetted mirror having semi-reflective facets, and also by optimizing the distance between the facetted mirror having semi-reflective facets and the annular facetted mirror having plane facets.

In accordance with the invention, unlike the prior art, the optical system no longer has a lens. Thus, each light module comprises a reduced number of elements. Thus, the axial lighting dome of the invention is lighter in weight. In addition, with this arrangement, its overall size can be reduced by 40%, it being possible for its thickness to be reduced from 12 cm to 7 cm while performing the same optical function. The positioning of the lighting dome is thus easier to adjust, thereby improving the comfort of the user.

In accordance with the invention, in the dome 9, there are provided a plurality of light modules M distributed about the illumination axis AA so that, for example, the LEDs 10 of the light modules M form a first ring about the illumination axis AA, and the LEDs 20 of the light modules M form a second ring about the axis AA so that the two rings are about the same axis. For example, the first ring of LEDs 10 has a diameter greater than the diameter of the second ring of LEDs 20. In the dome 9, there are therefore a series of beam splitters 13 distributed about the illumination axis AA and that form an annular facetted mirror having semi-reflective facets and arranged about the same axis as the rings of LEDs 10, 20. An annular facetted mirror having plane facets surrounds the annular facetted mirror having semi-reflective facets.

In accordance with the invention, the above-described construction principle of the lighting module M is used for implementing a lighting device 1 that is, in particular, in the form of a dome and with which it is possible to form an illumination spot 3 that is, in addition, of variable size in the working plane that corresponds to the operative field 4 that is about 1 m away from the dome.

In the embodiment in FIG. 6, and shown in alternating manner, there are provided light modules of types M1 and M2, with identical LED light sources, e.g. a first module M1 having first identical collimation optical systems 18, 19 that produce a spot of light of "small size" (this module being referred to as a "small spot" module) and a second module M2 having second identical collimation optical systems 18', 19' that produce a spot of light of "large size" (this module being referred to as a "large spot" module). The two modules are arranged in such a manner that the illumination spots are mutually superposed. The number of "small spot" modules M1 is not necessarily the same as the number of "large spot" modules M2. By means of this configuration, it is possible to cause the diameter of the illumination spot to vary without any mechanical movement, but rather by varying the feed currents of the LEDs in the two modules, while keeping a constant central illumination.

For this purpose, by means of the MCU 41, the electrical power supply 40 is controlled in such a manner as selectively to send currents I1, I2 respectively to the LEDs 10, 20 of the light modules M1 and currents I1', I2' respectively into the LEDs 10, 20 of the light modules M2 so as to modify the size of the illumination spot and/or so as to modify the color temperature as described above.

It should be understood that, in this arrangement, in order to keep the color temperature uniform in the illumination spot 3 of variable size, each light module M1 and M2 must emit the same color temperature. In other words, the ratio I1/I2 should be identical to the ratio I1'/I2' in order to obtain an illumination spot 3 at the intermediate color temperature Tkr, and said ratio is caused to vary in order to vary the color temperature in the illumination spot over the range Tk1 to Tk2. In order to vary the diameter of the illumination spot, the relative current between the light modules M1 and M2, i.e. the ratio I1/I1', and thus the ratio I2/I2', is caused to vary.

For a fixed intermediate color temperature Tkr between Tk1 and Tk2, it is possible to cause I1' and I1 or I2' and I2 to vary on the principle of communicating vessels so as to vary the diameter of the illumination spot between a large diameter (the diameter of the spot produced by the light modules M2 on their own) and a small diameter (the diameter of the spot produced by the light modules M1 on their own). It should be noted that the sum of the currents I1+I1' or I2+I2' must be substantially constant in order to have a variation in illumination spot diameter that is constant, while keeping the ratio I1/I2 equal to I1'/I2' so as to keep the same color temperature in the illumination spot 3.

More particularly, if the currents I1' and I2' are zero, the illumination spot 3 is produced by the light modules M1 on their own only, and so the illumination spot is small, with a diameter, for example, of 10 cm.

If the currents I1 and I2 are zero, the illumination spot 3 is produced by the light modules M2 on their own only, and so the illumination spot is large, with a diameter, for example, of 20 cm.

If non-zero currents I1 and I2 are delivered to the light modules M1 and non-zero currents I1' and I2' are delivered to the light modules M2, an illumination spot is produced with an intermediate diameter between 10 cm and 20 cm.

In order to keep the same level of illumination for the various illumination spot diameters, the MCU 41 adjusts the currents in all of the LEDs of the light modules M1 and M2 while keeping the ratio I1'/I2' identical to the ratio I1/I2 in such a manner as not to change the color temperature for the illumination spot 3. In order to go from an illumination spot of a certain diameter to a larger illumination spot, the MCU 41 must increase the currents in the same proportion for each LED.

In another embodiment shown in FIG. 8, in the dome 9, the modules M may form two rings of modules, both of which are on the central illumination axis AA.

The operating theater lighting device of the invention thus includes an axial lighting dome that is compact and that has a small number of parts, with light sources, an optical system and a power supply for feeding currents to the light sources, which optical system and which power supply are arranged to place the light beams coming from the sources in different superposition configurations of the light beams in the superposition plane that corresponds to the working plane in which the illumination spot is formed, these various configurations corresponding to different sizes or different diameters of the illumination spot.

Naturally, the present invention is in no way limited to the above description of one of its embodiments, which can undergo modifications without going beyond the ambit of the invention.

What is claimed is:

1. A lighting device for illuminating an operative field, the lighting device comprising:
    an axial lighting dome,
    a first ring of LEDs arranged about an axis in the axial lighting dome, said first ring of LEDs being suitable for emitting a first light beam at a first color temperature,
    a second ring of LEDs arranged about the same axis as said first ring of LEDs and suitable for emitting a second light beam at a second color temperature different from said first color temperature,
    an annular facetted mirror having semi-reflective facets and arranged about said axis for mixing said light beams emitted by said two rings of LEDs and for forming two resulting mixed light beams having the same intermediate color temperature lying between said first color temperature and said second color temperature,
    an annular optical system that surrounds said annular facetted mirror having semi-reflective facets so as to reflect said first resulting mixed light beam onto said operative field to combine it with said second resulting mixed light beam in a certain superposition configuration in a superposition plane in which an illumination spot is formed at said intermediate color temperature, wherein said annular optical system that surrounds said annular facetted mirror having semi-reflective facets is a total reflection annular facetted mirror having plane facets that are substantially geometrically similar to said semi-reflective facets, and
    collimation optical systems between each ring of LEDs and said annular facetted mirror having semi-reflective facets.

2. A lighting device according to claim 1, wherein said collimation optical systems are lenses.

3. A lighting device according to claim 1, wherein said collimation optical systems are collimators.

4. A lighting device according to claim 1, wherein said collimation optical systems are hybrid reflectors.

5. A lighting device according to claim 1, further comprising an electrical power supply for feeding currents to said LEDs and for modulating said currents.

6. A lighting device according to claim 5, wherein said electrical power supply for feeding currents to said LEDs, and for modulating said currents, is arranged to make it possible to modify at least one of the size of the illumination spot or the color temperature of the illumination spot.

7. A lighting device according to claim 5, wherein said electrical power supply is also arranged to modulate said currents in such a manner as to form an illumination spot at a constant illumination level.

8. A lighting device according to claim 1, wherein, in said first ring of LEDs, the LEDs are coupled in alternating manner to a first collimation optical system and to a second collimation optical system, said second collimation optical system being different from said first collimation optical system, and, in said second ring of LEDs, the LEDs are coupled in alternating manner to a third collimation optical system and to a fourth collimation optical system, said first and third collimation optical systems being identical, and said second and fourth collimation optical systems being identical, so that they form respectively a first illumination spot and a second illumination spot, the two spots being of different diameters.

9. A lighting device according to claim 1, wherein said annular facetted mirror having semi-reflective facets comprises a plurality of plane semi-reflective mirrors disposed annularly.

10. A lighting device according to claim 1, wherein said total-reflection annular facetted mirror having plane facets comprises a plurality of plane one-facet mirrors disposed annularly.

* * * * *